US 8,513,467 B2

(12) United States Patent
Dumesic et al.

(10) Patent No.: US 8,513,467 B2
(45) Date of Patent: Aug. 20, 2013

(54) PRODUCTION OF 2,4-DIONES FROM 4-HYDROXY-6-SUBSTITUTED-2-PYRONES

(75) Inventors: James A. Dumesic, Verona, WI (US); Mei Chia, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1 day.

(21) Appl. No.: 13/461,257

(22) Filed: May 1, 2012

(65) Prior Publication Data

US 2012/0283477 A1    Nov. 8, 2012

Related U.S. Application Data

(60) Provisional application No. 61/482,412, filed on May 4, 2011.

(51) Int. Cl.
*C07C 45/60* (2006.01)

(52) U.S. Cl.
USPC .......................................... 568/386; 568/391

(58) Field of Classification Search
USPC ................................................. 568/386, 391
See application file for complete search history.

(56) References Cited

PUBLICATIONS

Witter et al. (1948) "Colorimetric Determination of Acetylacetone and Related β-Diketones," *J. Biol. Chem.* 176:485-492.

*Primary Examiner* — Sikarl Witherspoon
(74) *Attorney, Agent, or Firm* — Joseph T. Leone, Esq.; DeWitt Ross & Stevens S.C.

(57) ABSTRACT

Described is a method of making 2,4-diones via acid catalyzed or thermally induced ring-opening of a 4-hydroxy-6-substituted-2-pyrone to yield a 2,4-dione.

20 Claims, No Drawings

PRODUCTION OF 2,4-DIONES FROM 4-HYDROXY-6-SUBSTITUTED-2-PYRONES

CROSS-REFERENCE TO RELATED APPLICATIONS

This application claims priority under 35 USC §119(e) to U.S. Provisional Patent Application 61/482,412 filed May 4, 2011, the entirety of which is incorporated herein by reference.

STATEMENT REGARDING FEDERALLY SPONSORED RESEARCH

This invention was made with government support under 0813570 awarded by the National Science Foundation. The government has certain rights in the invention.

FIELD OF THE INVENTION

The invention is directed to methods of making 2,4-diones via acid-catalyzed or thermally induced ring-opening of 4-hydroxy-6-substituted-2-pyrones.

BACKGROUND

Diones such as acetylacetone are commercially significant compounds. For example, acetylacetone is used as an intermediate to produce the bidentate ligand acetylacetonate (acac), which is widely used in organo-metallic catalysts. It is also used in various metal extraction processes, as an intermediate to make heterocyclic compounds, as a fuel additive, in dyes, and in metal plating processes, among other uses. The present inventors surmise that functionalized 2,4-diones will have similar commercial applications and importance as acetylacetone. Thus, there is potential commercial interest in making 2,4-diones such as acetylacetone from renewable sources.

Conventionally, acetylacetone is prepared industrially by the thermal rearrangement of isopropenyl acetate:

This is a multistep process starting with a reaction of acetone and ketene (both of which are derived from non-renewable petroleum feedstock) to yield the isopropenyl acetate. The subsequent rearrangement reaction is conducted at high temperature (typically 500° C. to 600° C.) over a metal catalyst, to yield the acetylacetone product.

Acetylacetone can also be made in laboratory quantities using acetone, acetic anhydride, and $BF_3$ as a catalyst:

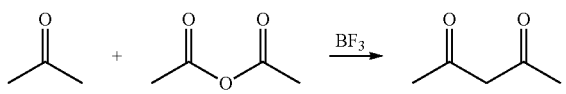

An alternative route involves the base-catalyzed condensation of acetone and ethyl acetate, followed by acidification.

Witter et al. describe a colorimetric assay for measuring acetylacetone that uses 1,2-diaminobenzene (i.e., o-phenylenediamine) as a binding partner. The resulting compound has a distinct reddish-purple color. See Witter et al. (1948) "Colorimetric Determination of Acetylacetone and Related β-Diketones," *J. Biol. Chem.* 176:485-492. The authors note that triacetic lactone will not bind with the 1,2-diaminobenzene, but that triacetic lactone can be converted to acetylacetone by hot acid hydrolysis. The acetylacetone so formed, however, must be simultaneously distilled from the boiling reaction mixture.

While these routes are straightforward, the required reactants (acetone, ethylacetate, and isopropenylacetate) are currently available solely from non-renewable, petroleum-based feedstock. Therefore, there remains an unmet need for a method to fabricate 2,4-diones such as acetylacetone in high yield from a renewable feedstock.

SUMMARY OF THE INVENTION

The present invention is directed to methods of making 2,4-diones via acid-catalyzed or thermally induced ring-opening of 4-hydroxy-6-substitited-2-pyrones.

One version of the invention comprises reacting a 4-hydroxy-6-substituted-2-pyrone to yield a corresponding 2,4-dione:

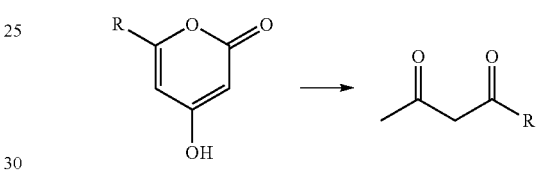

wherein "R" is selected from the group consisting of hydrogen; halo; hydroxyl; unsubstituted or halo-substituted, linear, branched, or cyclic alkyl, alkenyl, alkynyl, or alkoxy; unsubstituted or substituted aryl, aryl-$C_1$-$C_6$-alkyl, aryl-$C_1$-$C_6$-alkenyl, or aryl-$C_1$-$C_6$-alkynyl, wherein, if substituted, substituents are selected from the group consisting of halo, hydroxyl, acyl, acyloxy, and linear, branched, or cyclic alkyl, alkenyl, or alkynyl. The reacting is performed under conditions and for a time such that the corresponding 2,4-dione is formed.

Reacting the 4-hydroxy-6-substituted-2-pyrone can be performed in a number of solvents. In one version of the invention, the solvent is selected from the group consisting of water, $C_1$- to $C_6$-alcohols, and tetrahydrofuran. In other versions, the solvent is selected from the group consisting of water, tetrahydrofuran, and mixtures thereof. In yet other versions, the solvent is only water, only tetrahydrofuran, or only a mixture of water and tetrahydrofuran.

The reacting is preferably performed at a temperature of at least about 300 K, at a pressure from atmospheric to about 5 MPa, and/or under an inert atmosphere.

Some versions of the invention comprise reacting the 4-hydroxy-6-substituted-2-pyrone in the presence of a solid acid catalyst. The solid acid catalyst is preferably selected from the group consisting of a functionalized styrene-divinylbenzene copolymer and a functionalized tetrafluoroethylene-fluoropolymer copolymer.

Some versions of the invention comprise reacting the 4-hydroxy-6-substituted-2-pyrone in absence of an acid catalyst. In such methods, the reacting is preferably performed at a temperature of at least about 300 K.

Some versions of the invention comprise reacting the 4-hydroxy-6-substituted-2-pyrone in a reaction mixture without simultaneously separating the corresponding 2,4-dione from the reaction mixture.

The objects and advantages of the invention will appear more fully from the following detailed description of the preferred embodiment of the invention made in conjunction with the accompanying drawings.

DETAILED DESCRIPTION OF THE INVENTION

Described herein is a method of making 2,4-diones (2) via an acid-catalyzed or thermally induced ring-opening of a 4-hydroxy-6-R-2-pyrone (1):

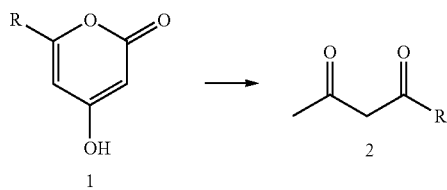

When "R" is methyl, 1 is 4-hydroxy-6-methyl-2-pyrone (HMP), and 2 is acetylacetone.

One version of the invention is a method to make 2,4-pentanedione and other 2,4-diones by reacting a 4-hydroxy-6-substituted-2-pyrone:

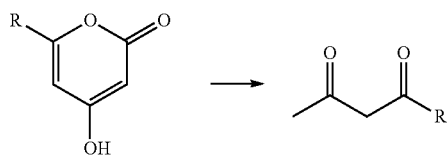

under conditions and for a time such that the corresponding 2,4-dione is formed. "R" can be selected from the group consisting of hydrogen, halo, hydroxyl, alkyl, alkenyl, alkynyl, alkoxy, aryl, aryl-$C_1$-$C_6$-alkyl, aryl-$C_1$-$C_6$-alkenyl, and aryl-$C_1$-$C_6$-alkynyl. The alkyl, alkenyl, alkynyl, and alkoxy can be unsubstituted or halo-substituted. The alkyl, alkenyl, alkynyl, and alkoxy also can be, linear, branched, or cyclic. The aryl group on the aryl-$C_1$-$C_6$-alkyl, aryl-$C_1$-$C_6$-alkenyl, and aryl-$C_1$-$C_6$-alkynyl can be unsubstituted or substituted. If substituted, the aryl group can include a halo; hydroxyl; acyl; acyloxy; and/or linear, branched, or cyclic alkyl, alkenyl, or alkynyl substituent. The $C_1$-$C_6$-alkyl, $C_1$-$C_6$-alkenyl, or $C_1$-$C_6$-alkynyl on the aryl-$C_1$-$C_6$-alkyl, aryl-$C_1$-$C_6$-alkenyl, and aryl-$C_1$-$C_6$-alkynyl can be unsubstituted or halo-substituted. The $C_1$-$C_6$-alkyl, $C_1$-$C_6$-alkenyl, and $C_1$-$C_6$-alkynyl on the aryl-$C_1$-$C_6$-alkyl, aryl-$C_1$-$C_6$-alkenyl, or aryl-$C_1$-$C_6$-alkynyl can also be linear, branched, or cyclic.

A primary advantage and benefit of the method described and claimed herein is that the 2,4-dione can be made in high yield from a renewable precursor, 4-hydroxy-6-substituted-2-pyrone (1).

In some versions of the invention, the reaction is carried out in the presence of a solid acid (heterogeneous) catalyst:

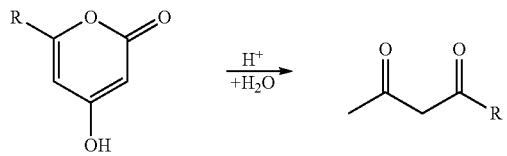

The solid acid catalysts for use in the method may comprise one or more solid acid materials without limitation, whether now known or developed in the future. The solid acid catalyst can be used independently as the only catalyst in the reaction. Alternatively, the solid acid catalyst can be utilized in combination with one or more mineral acids or other types of acid catalysts. Exemplary solid acid catalysts which can be utilized include, but are not limited to, heteropoly acids, acid resin-type catalysts, meso-porous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.), which may optionally be doped with additional acid groups such as sulfates, phosphates, etc., may also be used as solid acid catalysts.

Further examples of suitable solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. The functional group is generally of the sulfuric acid type. The Amberlyst®-brand resins are supplied as gellular or macro-reticular spherical beads. (Amberlyst® is a registered trademark of the Dow Chemical Co., Midland, Mich.) Similarly, Nafion®-brand resins are sulfonated tetrafluoroethylene-based fluoropolymer copolymers which are solid acid catalysts. Nafion® is a registered trademark of E.I. du Pont de Nemours & Co., Wilmington, Del.)

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

Particularly preferred solid acid catalysts are the functionalized styrene-divinylbenzene copolymers, exemplified by the Amberlyst®-brand resins.

The reaction is preferably carried out using water as the solvent. Other solvents, such as linear, branched, or cyclic alcohols (e.g., methanol, ethanol, propanol, isopropanol, sec-butanol, cyclobutanol, etc.) may also be used. Other suitable solvents include polar, aprotic solvents such as tetrahydrofuran, other linear or cyclic ethers, dimethyl sulfoxide, dimethylformamide, dioxane, etc. Mixtures of water and these solvents (and other suitable solvents) may also be used.

The reaction is preferably carried out at a temperature of at least about 300 K and more preferably at least about 353 K, such as about 373 K. Examples of suitable ranges include about 300 K to about 500 K and more preferably about 353.15 K to about 413.15 K (about 80° C. to about 140° C.). The reaction is also preferably carried out under an inert atmosphere ($N_2$, He, Ar, etc.) at atmospheric pressure or increased pressure, preferably from atmospheric up to about 5 MPa (atmospheric to about 725 psi). Temperatures and pressures above and below these preferred ranges are explicitly within the scope of the method.

In some versions, the reactant 1 is preferably present in the solvent in a concentration of from about 0.2 wt % to about 50 wt %, more preferably from about 0.2 wt % to about 25 wt %, and more preferably still from about 0.5 wt % to about 15 wt %. Concentrations above and below these preferred levels are explicitly within the scope of the method.

The ratio of the amount of reactant to the amount of catalyst will depend upon the chosen catalyst, the chosen solvent, and the temperature, pressure, and time under which the reaction is run. Optimal ratios can be determined empirically. When using water as the solvent, and Amberlyst® 70-brand resin as the catalyst, preferred ratios (reactant-to-catalyst, by mass) are typically from about 0.1-to-1 to 5-to-1, such as about 1-to-1 and about 2-to-1. Ratios above and below these levels are explicitly within the scope of the method.

In some versions of the invention, the reaction is carried out in the absence of an acid catalyst, whether a solid acid catalyst or a liquid catalyst. Versions in which the reactions are carried out in the absence of an acid catalyst preferably include water as a solvent and are carried out at a temperature of at least about 300 K.

The reactions described herein are capable of resulting in a percent conversion of 1 of at least about 20%, 30%, 40%, 50%, 60%, 70%, 75%, 80%, 85%, 90%, or 95%. The reactions described herein are also capable of resulting in a percent selectivity of yielding 2 of at least about 20%, 30%, 40%, 50%, 60%, 70%, 75%, 80%, 85%, 90%, 95%, or 99%. For example, the reaction performed in the presence of a solid acid catalyst and in water as a solvent results in a percent conversion of 1 of at least about 80%, 85%, 90%, or 95% and a percent selectivity of yielding 2 of at least about 80%, 85%, 90%, 95%, or 99%. The reaction performed in the absence of a solid acid catalyst and in water as a solvent results in a percent conversion of 1 of at least about 80%, 85%, 90%, or 94% and a percent selectivity of yielding 2 of at least about 80%, 85%, 90%, or 95%. The reaction performed in the presence of a solid acid catalyst and in tetrahydrofuran as a solvent results in a percent conversion of 1 of at least about 20%, 30%, 40%, 50%, 60%, or 62% and a percent selectivity of yielding 2 of at least about 20%, 30%, 40%, 50%, 60%, or 65%.

The above percent conversions of 1 and percent selectivities of yielding 2 can be obtained in the present methods without distilling or otherwise separating the product 2 from the reaction mixture while the reaction is proceeding. Accordingly, some versions of the invention include reacting the 4-hydroxy-6-substituted-2-pyrone (1) to the corresponding 2,4-dione (2) in a reaction mixture without simultaneously separating (e.g., distilling) the 2,4-dione (2) from the reaction mixture, wherein the reacting results in any of the percent conversions of 1 and percent selectivities of yielding 2 mentioned above.

In the Examples, the exemplary reactions were run in batch fashion. The method, however, may be run in batch, semi-continuous, or continuous reactions.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present invention shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

The methods of the present invention can comprise, consist of, or consist essentially of the essential elements and limitations of the method described herein, as well as any additional or optional ingredients, components, or limitations described herein or otherwise useful in synthetic organic chemistry.

It is understood that the invention is not confined to the particular construction and arrangement of parts herein illustrated and described, but embraces such modified forms thereof as come within the scope of the following claims.

EXAMPLES

The following Examples are included solely to provide a more detailed description of the invention disclosed and claimed herein. The Examples do not limit the scope of the claims in any fashion.

General Methods:

Quantification was performed using a gas chromatograph (Shimadzu GC-2010; Shimadzu Scientific Instruments, Columbia, Md.) equipped with a flame-ionization detector (FID). Identification of products in the liquid phase was performed using a gas chromatograph-mass spectrometer (Shimadzu Corp., GCMS-QP2010S) equipped with a Rxi®-brand SHRXI-5MS capillary column (30 m×0.25 mm×0.25 µm) (Restek Corporation, Bellefonte, Pa.). Gas phase products were collected in a gas bag and analyzed using a Carle gas chromatograph (Series 400 AGC; Carle Instruments, Inc. Gaithersburg, Md., now defunct) equipped with a thermal conductivity detector (TCD) and a Porapak® Q-brand packed column (Alltech Associates, Inc., Deerfield, Ill.), and a Varian gas chromatograph (Saturn 3; Varian, Inc., a wholly-owned subsidiary of Agilent Technologies, Inc., Santa Clara, Calif.) equipped with a FID and a GS-Q column (J&W Scientific, also a wholly-owned subsidiary of Agilent).

Reaction Using Water or Tetrahyrofuran as Solvent:

The reactions were carried out in a 50-mL batch reactor, at 100° C., under an inert atmosphere, at elevated pressure (~3 MPa). The batch reaction time was 1-16 h. Detailed results are shown in Table 1. An initial reactant mixture of 0.8-1.8 wt % 4-hydroxy-6-methyl-2-pyrone (1, $R=CH_3$) dissolved in a solvent was employed. Specifically, the hydration and decarboxylation of 4-hydroxy-6-methyl-2-pyrone (1, $R=CH_3$) proceeded over Amberlyst® 70-brand catalyst at a mass ratio of 4-hydroxy-6-methyl-2-pyrone:catalyst=2:1.

TABLE 1

Ring-opening and decarboxylation of 4-hydroxy-6-methyl-2-pyrone (1, $R=CH_3$) to 2,4-pentanedione (2, $R=CH_3$).[a]

| Entry | Solvent | Feed concentration (wt %) | Time (h) | Conversion of 1 ($R=CH_3$) (%) | Selectivity to 2 ($R=CH_3$) (%) |
|---|---|---|---|---|---|
| 1 | Water | 0.8 | 1 | 68.5 | 78.1 |
| 2 | Water | 0.8 | 4 | 95.3 | >99 |
| 3 | Water[b] | 0.8 | 1 | 77.1 | 81.7 |
| 4 | Water[b] | 0.8 | 4 | 94.3 | 95.6 |
| 5 | THF | 1.8 | 4 | 23.6 | 71.5 |
| 6 | THF | 1.8 | 16 | 62.4 | 65.3 |
| 7 | THF[c] | 1.8 | 4 | 3.3 | >99 |
| 8 | THF[b] | 1.8 | 4 | 5.5 | 0.0 |

[a]Batch reactions. Reaction conditions: 373 K, 21 bar He, Amberlyst ™ 70 as catalyst, mass ratio 4-hydroxy-6-methyl-2-pyrone:catalyst = 2:1.
[b]No catalyst.
[c]Catalyst dried at 373 K prior to reaction.

Using water as the solvent, 95% conversion of 4-hydroxy-6-methyl-2-pyrone was achieved with quantitative selectivity to the desired 2,4-pentanedione (2, R=CH$_3$) product (Table 1, Entry 2). Under identical reaction conditions using tetrahydrofuran as the solvent, 62% conversion of 4-hydroxy-6-methyl-2-pyrone (1, R=CH$_3$) was achieved, with 65% selectivity to the desired 2,4-pentanedione (2, R=CH$_3$) product (Table 1, Entry 6). The reaction can also be accomplished in water without the aid of a catalyst (Table 1, Entries 3 and 4), where close to quantitative yields of desired 2,4-pentanedione (2, R=CH$_3$) product can be similarly achieved.

What is claimed is:

1. A method of making 2,4-diones, the method comprising reacting a 4-hydroxy-6-substituted-2-pyrone to yield a corresponding 2,4-dione:

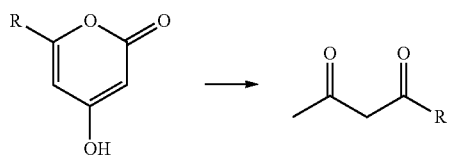

wherein "R" is selected from the group consisting of hydrogen; halo; hydroxyl; unsubstituted or halo-substituted, linear, branched, or cyclic alkyl, alkenyl, alkynyl, or alkoxy; unsubstituted or substituted aryl, aryl-C$_1$-C$_6$-alkyl, aryl-C$_1$-C$_6$-alkenyl, or aryl-C$_1$-C$_6$-alkynyl, wherein, if substituted, substituents are selected from the group consisting of halo, hydroxyl, acyl, acyloxy, and linear, branched, or cyclic alkyl, alkenyl, or alkynyl, under conditions and for a time such that the corresponding 2,4-dione is formed.

2. The method of claim 1, comprising reacting the 4-hydroxy-6-substituted-2-pyrone in a solvent selected from the group consisting of water, C$_1$- to C$_6$-alcohols, and tetrahydrofuran.

3. The method of claim 1, comprising reacting the 4-hydroxy-6-substituted-2-pyrone in a solvent selected from the group consisting of water, tetrahydrofuran, and mixtures thereof.

4. The method of claim 1, comprising reacting the 4-hydroxy-6-substituted-2-pyrone in a solvent wherein the solvent is water.

5. The method of claim 1, comprising reacting the 4-hydroxy-6-substituted-2-pyrone in a solvent wherein the solvent is tetrahydrofuran.

6. The method of claim 1, comprising reacting the 4-hydroxy-6-substituted-2-pyrone in a solvent wherein the solvent is a mixture of water and tetrahydrofuran.

7. The method of claim 1, comprising reacting the 4-hydroxy-6-substituted-2-pyrone in the presence of a solid acid catalyst.

8. The method of claim 1, comprising reacting the 4-hydroxy-6-substituted-2-pyrone in the presence of a solid acid catalyst selected from the group consisting of a functionalized styrene-divinylbenzene copolymer and a functionalized tetrafluoroethylene-fluoropolymer copolymer.

9. The method of claim 1, comprising reacting the 4-hydroxy-6-substituted-2-pyrone at a temperature of at least about 300 K.

10. The method of claim 1, comprising reacting the 4-hydroxy-6-substituted-2-pyrone at a pressure from atmospheric to about 5 MPa.

11. The method of claim 1, comprising reacting the 4-hydroxy-6-substituted-2-pyrone under an inert atmosphere.

12. The method of claim 1, comprising reacting the 4-hydroxy-6-substituted-2-pyrone in absence of an acid catalyst.

13. The method of claim 1, comprising reacting the 4-hydroxy-6-substituted-2-pyrone at a temperature of at least about 300 K in absence of an acid catalyst.

14. The method of claim 1, comprising reacting the 4-hydroxy-6-substituted-2-pyrone in a reaction mixture without simultaneously separating the corresponding 2,4-dione from the reaction mixture.

15. A method of making 2,4-diones, the method comprising reacting a 4-hydroxy-6-substituted-2-pyrone in the presence of a solid acid catalyst to yield a corresponding 2,4-dione:

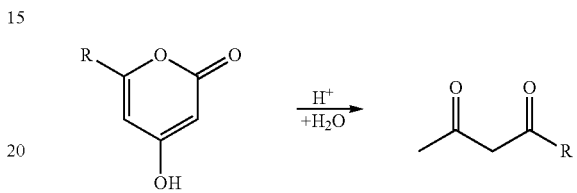

wherein "R" is selected from the group consisting of hydrogen; halo; hydroxyl; unsubstituted or halo-substituted, linear, branched, or cyclic alkyl, alkenyl, alkynyl, or alkoxy; aryl-unsubstituted aryl, aryl-C$_1$-C$_6$-alkyl, aryl-C$_1$-C$_6$-alkenyl, or aryl-C$_1$-C$_6$-alkynyl; and aryl-substituted aryl, aryl-C$_1$-C$_6$-alkyl, aryl-C$_1$-C$_6$-alkenyl, or aryl-C$_1$-C$_6$-alkynyl comprising a halo, hydroxyl, acyl, acyloxy, linear, branched or cyclic alkyl, alkenyl, or alkynyl substituent,
under conditions and for a time such that the corresponding 2,4-dione is formed.

16. The method of claim 15, wherein the solid acid catalyst is selected from the group consisting of a functionalized styrene-divinylbenzene copolymer and a functionalized tetrafluoroethylene-fluoropolymer copolymer.

17. The method of claim 15, comprising reacting the 4-hydroxy-6-substituted-2-pyrone in a reaction mixture without simultaneously separating the corresponding 2,4-dione from the reaction mixture.

18. A method of making 2,4-diones, the method comprising reacting a 4-hydroxy-6-substituted-2-pyrone in the absence of an acid catalyst to yield a corresponding 2,4-dione:

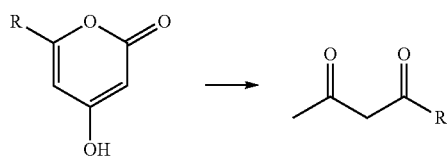

wherein "R" is selected from the group consisting of hydrogen; halo; hydroxyl; unsubstituted or halo-substituted, linear, branched, or cyclic alkyl, alkenyl, alkynyl, or alkoxy; aryl-unsubstituted aryl, aryl-C$_1$-C$_6$-alkyl, aryl-C$_1$-C$_6$-alkenyl, or aryl-C$_1$-C$_6$-alkynyl; and aryl-substituted aryl, aryl-C$_1$-C$_6$-alkyl, aryl-C$_1$-C$_6$-alkenyl, or aryl-C$_1$-C$_6$-alkynyl comprising a halo, hydroxyl, acyl, acyloxy, linear, branched or cyclic alkyl, alkenyl, or alkynyl substituent,
under conditions and for a time such that the corresponding 2,4-dione is formed.

19. The method of claim 18, comprising reacting the 4-hydroxy-6-substituted-2-pyrone at a temperature of at least about 300 K.

20. The method of claim 18, comprising reacting the 4-hydroxy-6-substituted-2-pyrone in a reaction mixture without simultaneously separating the corresponding 2,4-dione from the reaction mixture.

* * * * *